United States Patent
Riondel et al.

(10) Patent No.: US 8,431,716 B2
(45) Date of Patent: Apr. 30, 2013

(54) PREPARATION OF ALKYLIMIDAZOLIDONE (METH)ACRYLATES IN WATER

(75) Inventors: Alain Riondel, Forbach (FR); Jean-Michel Paul, Metz (FR)

(73) Assignee: Arkema France, Colombes (FR)

( * ) Notice: Subject to any disclaimer, the term of this patent is extended or adjusted under 35 U.S.C. 154(b) by 359 days.

(21) Appl. No.: 12/988,351

(22) PCT Filed: Apr. 8, 2009

(86) PCT No.: PCT/FR2009/050615
§ 371 (c)(1),
(2), (4) Date: Nov. 11, 2010

(87) PCT Pub. No.: WO2009/136073
PCT Pub. Date: Nov. 12, 2009

(65) Prior Publication Data
US 2011/0049423 A1     Mar. 3, 2011

(30) Foreign Application Priority Data
Apr. 17, 2008   (FR) .................................... 08 52594

(51) Int. Cl.
*C07D 233/32*    (2006.01)
*C07D 233/30*    (2006.01)
*C07D 233/70*    (2006.01)
*C07D 233/02*    (2006.01)
*C09K 3/00*      (2006.01)

(52) U.S. Cl.
USPC ........ 548/324.1; 540/460; 540/494; 544/318; 252/182.13; 252/182.29; 252/183.12

(58) Field of Classification Search ............. 548/324.1; 544/318; 540/460, 492; 252/182.13, 182.29, 252/183.12
See application file for complete search history.

(56) References Cited

U.S. PATENT DOCUMENTS

| | | |
|---|---|---|
| 5,210,199 A | 5/1993 | Grosius et al. |
| 5,498,723 A | 3/1996 | Riondel et al. |
| 5,610,313 A * | 3/1997 | Riondel et al. ............. 548/324.1 |
| 5,637,689 A * | 6/1997 | Herbst et al. ................. 540/460 |
| 6,509,494 B1 | 1/2003 | Weir |
| 6,515,138 B2 | 2/2003 | Weir et al. |
| 6,706,887 B2 * | 3/2004 | Paul et al. ................. 548/324.1 |
| 2003/0096931 A1 * | 5/2003 | Paul et al. ..................... 526/258 |
| 2006/0173191 A1 | 8/2006 | Curtis |
| 2010/0219371 A1 * | 9/2010 | Paul ......................... 252/182.29 |

* cited by examiner

*Primary Examiner* — Joseph D Anthony
(74) *Attorney, Agent, or Firm* — Lynn B. Morreale

(57) ABSTRACT

The invention relates to special (methyl)acrylaic monomers and concerns more particularly an enhanced process for preparing solutions of alkylimiozolidone (meth)acrylates in water solutions of alkylimidazolidone (meth)acrylates in a light (meth)acrylate.

5 Claims, No Drawings

PREPARATION OF ALKYLIMIDAZOLIDONE (METH)ACRYLATES IN WATER

FIELD OF THE INVENTION

The invention relates to special (meth)acrylic monomers and relates more particularly to an improved process for preparing solutions of alkylimidazolidone (meth)acrylates in water.

PRIOR ART

Alkylimidazolidone (meth)acrylates are known for their role in the composition of polymers which can be used as coatings and adhesives, in the field of paper and textiles, for their use as leather treatment agents and in the production of emulsion paints.

From documents EP 1 293 502, EP 433 135, EP 712 846, EP 650 962 or EP 619 309 for example, it is known to prepare alkylimidazolidone acrylates or methacrylates (denoted by (meth)acrylates) of formula (I):

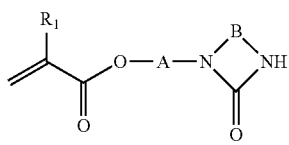

in which $R_1$ is a hydrogen atom or a methyl group and A and B represent, independently of one another, a straight- or branched-chain alkylene group having from 2 to 5 carbon atoms,
according to a transesterification process by reaction of at least one alkyl(meth)acrylate of formula (II):

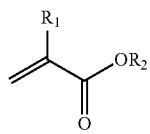

in which $R_1$ has the abovementioned meaning and $R_2$ is a straight- or branched-chain alkyl group having from 1 to 4 carbon atoms,
with a heterocyclic alcohol of formula (III):

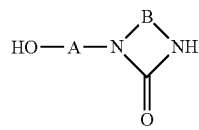

in which A and B have the abovementioned meanings,
in the presence of a catalyst, and generally in the presence of a polymerization inhibitor.

When the (meth)acrylate (II) is in large excess with respect to the heterocyclic alcohol (III), a composition is obtained at the end of the reaction which comprises a solution of alkylimidazolidone (meth)acrylate of formula (I) in the (meth)acrylate (II).

Thus, alkylimidazolidone (meth)acrylates are generally sold in a light (meth)acrylate (II). More particularly, 1-ethylimidazolyl-2-one methacrylate (EIOM), prepared from methyl methacrylate (MMA), is sold in solution in methyl methacrylate (MMA).

However, alkylimidazolidone (meth)acrylates in solution in a light (meth)acrylate, such as methyl methacrylate, exhibit drawbacks when they are employed. In particular, depending on the final use, the methyl methacrylate has a low vapor pressure and results in the emission of volatile organic compounds (VOCs).

It is known to replace methyl methacrylate by water in compositions comprising an alkylimidazolidone (meth)acrylate and methyl methacrylate obtained according to a transesterification process in the presence of a polymerization inhibitor.

According to document EP 1 241 163, solutions of 1-ethylimidazolyl-2-one methacrylate in MMA are prepared by transesterification in the presence of 4-hydroxy-2,2,6,6-tetramethylpiperidinyloxy (4-hydroxy TEMPO) as polymerization inhibitor. Then the method of replacing MMA with water consists in removing virtually all the methyl methacrylate by vacuum distillation under temperature/pressure conditions of 40° C. to 60° C./760 to 60 mmHg, and then, after having cooled the product to a temperature of 60° C.-70° C., in adding water while continuing to stir the mixture for 15 minutes. Polymerization inhibitor is not added for this step. The final composition obtained comprises more than 50% of water but still more than 2% of residual methyl methacrylate.

According to document EP 902 017, the method consists in removing the methyl methacrylate by distillation in the form of an azeotrope with water while continuously introducing water into the mixture comprising the alkylimidazolidone (meth)acrylate and the methyl methacrylate. The final composition obtained comprises approximately 48% of water and less than 1% of residual methyl methacrylate. However, this process involves the distillation of large amounts of MMA/water azeotrope and requires a decantation, then a vacuum filtration of the final product in order to obtain a clear product.

An improved process has now been found for replacing the light (meth)acrylate with water in formulations of alkylimidazolidone (meth)acrylates in a light (meth)acrylate. The improvement of the process consists in removing a sufficient amount of light (meth)acrylate by distillation before continuously introducing water and continuing the removal of the light (meth)acrylate in the form of a light (meth)acrylate/water azeotrope. Moreover, the distillation of the light (meth) acrylate is carried out after addition of an effective amount of at least one polymerization inhibitor with the exception of derivatives of 2,2,6,6-tetramethyl-1-piperidinyloxy (TEMPO). Indeed, the presence of a TEMPO derivative may adversely affect the coloration of the monomer, and it is detrimental to the use of the final solution of alkylimidazolidone (meth)acrylate in water, especially to its reactivity in order to prepare polymers based on alkylimidazolidone (meth)acrylate.

This operating method thus makes it possible to overcome the drawbacks of the aforementioned existing processes while manufacturing a thermally stable product without using a compound that is harmful for the final use of the product obtained.

The objective of the present invention is therefore to provide a process for preparing solutions of alkylimidazolidone (meth)acrylates in water which is simple and rapid (comprising the least number of steps possible, such as decantation or filtration), with reduced energy requirements and that results in a high-quality product with improved productivity.

DESCRIPTION OF THE INVENTION

The subject of the present invention is therefore a process for preparing solutions, in water, of an alkylimidazolidone (meth)acrylate of formula (I):

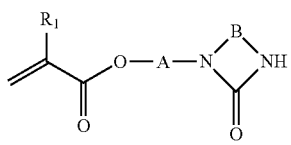

in which $R_1$ is a hydrogen atom or a methyl group and A and B represent, independently of one another, a straight- or branched-chain alkylene group having from 2 to 5 carbon atoms,
from solutions of an alkylimidazolidone (meth)acrylate of formula (I) in a light (meth)acrylate of formula (II):

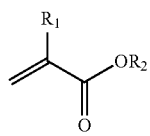

in which $R_1$ is a hydrogen atom or a methyl group and $R_2$ is a straight- or branched-chain alkyl group having from 1 to 4 carbon atoms, characterized in that it comprises the following steps:
(a) adding, to the initial solution, from 100 to 2000 ppm of at least one polymerization inhibitor, with the exception of 2,2,6,6-tetramethyl-1-piperidinyloxy derivatives;
(b) removing, by distillation under reduced pressure, from 75 to 95% by weight of the (meth)acrylate of formula (II) present in the initial solution;
(c) continuously adding water at the same time as the distillation is continued in order to remove the remaining (meth)acrylate of formula (II) in the form of a (meth) acrylate of formula (II)/water azeotrope; and
(d) bringing the mixture obtained in (c) back to atmospheric pressure and to ambient temperature and introducing an amount of water in order to adjust the water content of the final solution.

The initial solution of alkylimidazolidone (meth)acrylate of formula (I) in the light (meth)acrylate (II) generally contains from 20 to 80% by weight expressed as alkylimidazolidone (meth)-acrylate of formula (I) with monomeric byproducts bearing a ureido functional group, relative to the initial solution, preferably from 30 to 60% by weight, and more particularly from 45 to 55% by weight. The monomeric byproducts bearing a ureido functional group are the byproducts inherent in the manufacture of the alkylimidazolidone (meth)acrylate of formula (I) via transesterification. They result from the Michael addition of the secondary amine functional group of the imidazolidone ring to another molecule of alkylimidazolidone (meth)acrylate (I) or to a molecule of alkyl (meth)acrylate (II). Generally, these byproducts are present at a content ranging from 5 to 25% relative to the alkylimidazolidone (meth)acrylate, in particular from 10 to 20%.

As examples of compound (I), mention may be made of those for which the A group is an alkylene group having carbon atoms, and more particularly 1-ethyl-imidazolidyl-2-one methacrylate (EIOM).

Preferably, the (meth)acrylate (II) is a light (meth)acrylate such as methyl (meth)acrylate or ethyl (meth)acrylate, which has a content ranging from 20 to 80% in the initial solution, particularly from 40 to 70%, more specifically from 15 to 55% by weight in the initial solution.

The initial solutions of alkylimidazolidone (meth)acrylate of formula (I) in a light (meth)acrylate of formula (II) may be obtained according to one of the processes known to a person skilled in the art, such as those mentioned previously, or are available commercially.

The process according to the invention consists in replacing the light (meth)acrylate of formula (II) with water, in four steps.

The first step (a) consists in loading the initial solution of alkylimidazolidone (meth)acrylate in the light (meth)acrylate into a reactor and in adding one or more polymerization inhibitors apart from derivatives of 2,2,6,6-tetramethyl-1-piperidinyloxy (TEMPO). It is possible to add, for example, phenothiazine, hydroquinone, hydroquinone monomethyl ether, di-tert-butyl-para-cresol, para-phenylenediamine or di-tert-butylcatechol. The content of polymerization inhibitors is generally between 100 and 2000 ppm in the solution, preferably from 200 to 800 ppm.

The second step (b) consists in distilling a portion of the light (meth)acrylate. Advantageously, from 75 to 95% of the light (meth)acrylate present in the solution of alkylimidazolidone (meth)acrylate, and preferably from 80 to 90%, are distilled during this step. Generally, the distillation is carried out at a temperature ranging from 35° C. to 65° C., preferably from 40° C. to 55° C., under a pressure between 50 and 80 mmHg, over 1 to 5 hours.

Next, the third step (c) consists in continuously introducing water, while continuing the distillation of the light (meth) acrylate. Generally, the amount of water necessary in order to distill the remaining light (meth)acrylate in azeotropic form is added, i.e. an amount of water ranging from 10% to 50%, preferably from 15% to 40% expressed relative to the initial light (meth)acrylate. The water is preferably supplemented with at least one polymerization inhibitor, generally chosen from those already added to the initial solution. The addition is carried out continuously over a duration which may range from 0.5 to 3 hours, under a pressure of 60 to 80 mmHg, and at a temperature ranging from 35° C. to 50° C.

During this third step, the light (meth)acrylate/water azeotrope is removed and the residual content of (meth)acrylate (II) in the solution obtained is generally less than 0.5%, or even less than 0.2%. It is not therefore necessary to carry out a final stripping, in order to complete the removal of the light compound. This step, due to the limited amount of light (meth)acrylate to be removed, does not require the use of large amounts of water and consequently does not last for a long time.

During these two steps (b) and (c), bubbling with air, optionally depleted air (8 to 9% $O_2$ by volume), is advantageously carried out.

At the end of the third step, during step (d), the solution is brought back to atmospheric pressure and to ambient temperature, and an amount of water is added so as to obtain a final solution comprising from 40 to 60% water, preferably from 45 to 55% water. The water content may be determined easily using a thermobalance.

The solutions in water thus obtained remain stable over a long period and can be used for preparing special (meth) acrylic polymers.

The following examples illustrate the present invention without however limiting the scope thereof.

Exemplary Embodiments

The following abbreviations are used therein:
HEIO: 1-(2-hydroxyethyl)imidazolidyl-2-one
EIOM: 1-ethylimidazolidyl-2-one methacrylate
NORSOCRYL® 104: 50 wt % solution of 1-ethyl-imidazolidyl-2-one methacrylate and of monomeric impurities of ureido type in methyl methacrylate
MMA: methyl methacrylate
HQME: hydroquinone methyl ether
PTZ: phenothiazine
The percentages are expressed as weight percentages.

Example 1

According to the Invention

Use is made, as apparatus, of a jacketed 1-1 glass reactor equipped with an adiabatic column having multiknit packing (around 12 plates) surmounted by a reflux head, with two probes for measuring the temperature at the top of the column and in the reactor, with a variable speed mechanical stirrer, and with a dropping funnel. The heating is provided by an oil bath.

The reactor is charged with 1114 g of Norsocryl® 104 (N104) and 0.409 g of HQME (367 ppm relative to the N104). The composition of N104 is the following:
HEIO: 0.7%;
EIOM: 40.8%;
MMA: 50.2%;
HQME: 92 ppm;
PTZ: 411 ppm;
other products: 3.7%.

Air bubbling is maintained within the charge and the following operating conditions are used in order to distill the MMA contained in the N104:
P: 75 mmHg
Temperature of the reactor: 41 to 57° C. (maximum temperature set at 65° C.)
Temperature at the top of the column: 35° C. max
Reflux ratio: 1:1
Time: 1 h 30 min
476.6 g of MMA is distilled, which is equivalent to 85.2% of the MMA present.

When the flow at the top of the column is almost zero, the water begins to be introduced, i.e. 210.4 g of water supplemented with 0.322 g of HQME (i.e. 1530 ppm) added over a period of 30 minutes, under the following conditions:
P: 75 mmHg
Temperature of the reactor: 40 to 46° C.
Temperature at the top of the column: 28-40° C.
Reflux ratio: 10/1

At the end of this step, which lasts 1 hour, the MMA/water azeotrope is distilled, and when the temperature at the top of the column is aligned with that of the water, 40 g of water is distilled in order to fully deplete the MMA at the bottom, over 1 hour and with a reflux ratio of 10/1.

The distillate settles into two phases, 55 g of MMA is recovered in the upper phase and 60 g of lower aqueous phase.

After shutting down the heating, the reactor is returned to atmospheric pressure. And after returning to ambient temperature, 160.7 g of water are added and the water content is monitored using a thermobalance. Next the addition of water is completed in order to obtain a water content of around 48%. 55.7 g of water were added, which led to a final water content of 48.3%.

960 g of a solution is recovered, HPLC analysis of which indicates the following composition:
HEIO: 1.3%;
EIOM: 46.6%;
MMA: 0.2%;
HQME: 754 ppm;
PTZ: 409 ppm;
water: 48.3%;
other products: 3.7%.

The solution obtained is stable and no polymerization is observed after 12 days being held at a temperature of 60° C.

Example 2

Comparative

The operating conditions from example 1 are reproduced, except that, all other things being equal, 532 g of the MMA (i.e. 95%) present in the initial N104 are removed, over a period of 1 h 45 min. Under these conditions, the stability of the aqueous solution obtained is less than 24 h.

Example 3

Comparative

The operating conditions from example 1 are reproduced, except that, all other things being equal, 391.5 g of the MMA (i.e. 70%) present in the initial N104 are removed, over a period of one hour. Under these conditions, the time for removing the MMA/water azeotrope is 4 h 30 min, which results in a reduction in the productivity of around 40%.

The invention claimed is:
1. A process for preparing solutions, in water, of an alkylimidazolidone (meth)acrylate of formula (I):

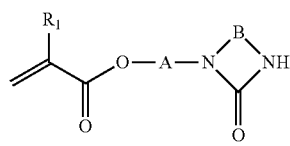

in which $R_1$ is a hydrogen atom or a methyl group and A and B represent, independently of one another, a straight-chain alkylene group or branched-chain alkylene group having from 2 to 5 carbon atoms,
from solutions of an alkylimidazolidone (meth)acrylate of formula (I) in a light (meth)acrylate of formula (II):

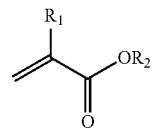

in which $R_2$ is a straight- or branched-chain alkyl group having from 1 to 4 carbon atoms, characterized in that it comprises the following steps:
(a) adding, to an initial solution of an alkylimidazolidone (meth)acrylate of formula (I), from 100 to 2000 ppm of at least one polymerization inhibitor, with the exception of 2,2,6,6-tetramethyl-1-piperidinyloxy derivatives;

(b) removing, by distillation under reduced pressure, from 75 to 95% by weight of the (meth)acrylate of formula (II) present in the initial solution;

(c) continuously adding water at the same time as the distillation is continued in order to remove the remaining (meth)acrylate of formula (II) in the form of a (meth)acrylate of formula (II)/water azeotrope; and (d) bringing the mixture obtained in (c) back to atmospheric pressure and to ambient temperature and introducing an amount of water in order to adjust the water content of the final solution.

2. The process as claimed in claim 1, characterized in that the compound of formula (I) is 1-ethyl-imidazolidyl-2-one methacrylate.

3. The process as claimed in claim 1, characterized in that, in step (b), from 80 to 90% by weight of the (meth)acrylate of formula (II) present in the initial solution is distilled.

4. The process as claimed in claim 1, characterized in that the amount of water added continuously in step (c) ranges from 10% to 50% expressed relative to the initial light (meth)acrylate.

5. The process as claimed in claim 1, characterized in that the water content of the final solution is adjusted to 40% to 60%.

* * * * *